(12) United States Patent
Lacoste et al.

(10) Patent No.: US 9,033,886 B2
(45) Date of Patent: May 19, 2015

(54) ULTRASOUND TREATMENT DEVICE (75) Inventors: Francois Lacoste, Paris (FR); Sylvain Yon, Bagneux (FR)

(73) Assignee: Theraclion SAS, Paris (FR)

(*) Notice: Subject to any disclaimer, the term of this patent is extended or adjusted under 35 U.S.C. 154(b) by 145 days.

(21) Appl. No.: 13/514,326

(22) PCT Filed: Dec. 7, 2010

(86) PCT No.: PCT/EP2010/069014
§ 371 (c)(1),
(2), (4) Date: Jun. 7, 2012

(87) PCT Pub. No.: WO2011/069985
PCT Pub. Date: Jun. 16, 2011

(65) Prior Publication Data
US 2012/0238873 A1  Sep. 20, 2012

(30) Foreign Application Priority Data
Dec. 10, 2009 (EP) .................... 09178640

(51) Int. Cl.
A61B 8/00 (2006.01)
A61N 7/02 (2006.01)
A61B 19/00 (2006.01)

(52) U.S. Cl.
CPC ............ *A61N 7/02* (2013.01); *A61B 8/4461* (2013.01); *A61B 2019/5276* (2013.01)

(58) Field of Classification Search
CPC . A61N 7/02; A61B 2019/5276; A61B 8/4461
See application file for complete search history.

(56) References Cited

U.S. PATENT DOCUMENTS

| 5,178,135 A | 1/1993 | Uchiyama et al. |
| 6,425,867 B1 | 7/2002 | Vaezy et al. |
| 2004/0254620 A1 | 12/2004 | Lacoste et al. |
| 2005/0203399 A1 | 9/2005 | Vaezy et al. |
| 2006/0173307 A1* | 8/2006 | Amara et al. ................ 600/437 |
| 2007/0118057 A1 | 5/2007 | Ein-Gal |

FOREIGN PATENT DOCUMENTS

| WO | 89/07909 | 9/1989 |
| WO | 03/008041 | 1/2003 |
| WO | 2007/022484 | 2/2007 |

* cited by examiner

*Primary Examiner* — Mark Remaly
(74) *Attorney, Agent, or Firm* — Davis & Bujold, P.L.L.C.; Michael J. Bujold (57) ABSTRACT

The invention concerns a device for treatment of an organ or tissue of a living being. The device comprises at least one treatment transducer for emission of ultrasound waves, preferably high intensity focused ultrasound (HIFU) waves, focusable on a focal point within or on the surface of said organ or tissue, as well as means for rotating said treatment transducer around an axis which intersects said focal point. The device further comprises synchronization means for synchronizing the rotation of the treatment transducer with at least the emission of ultrasound waves from said treatment transducer and/or an additional imaging transducer.

6 Claims, 5 Drawing Sheets

ULTRASOUND TREATMENT DEVICE

The present invention relates to a device for treatment of an organ or tissue of a living being with ultrasound, preferably high intensity focused ultrasound (HIFU) waves, according to claim 1.

Treatment with ultrasound waves, particularly high intensity focused ultrasound (HIFU) is well known in the art. It is especially used for treatment of tumours of the thyroid, breast, uterus and prostate. Tumours are thereby destroyed by means of thermal energy. The necessary heat is generated by focussing high intensity ultrasound waves onto a focal point. As an acoustic wave propagates through the tissue, part of it is absorbed and converted to heat. At the focal point, due to the significant energy concentration, the temperature within the tissue rises to 65° to 85° C., destroying the diseased tissue by coagulation necrosis. One big advantage of treatment with HIFU is that it is a non-invasive treatment method, thereby considerably reducing risks for the patient.

HIFU treatment devices usually comprise a treatment head with a HIFU transducer. The treatment head is placed on the tissue to be treated or on tissue adjacent to the organ to be treated. Such devices are sold e.g. by EDAP TMS under the trademark Ablatherm® or by Theraclion under the name TH-One.

When treating an internal organ, such as the thyroid, the ultrasound waves generally travel through a layer of healthy tissue before reaching the focal zone. The travelling ultrasound waves also generate heat within this healthy tissue, which may accumulate, leading to damage or even necrosis. This can be avoided by delivering the ultrasound radiation in short pulses separated by a blanking period which allows the healthy tissue to cool down between pulses thus avoiding heat damage. On the other hand, heat generated by the pulses in the focal zone is high enough to produce tissue damage, despite of the cooling phases between two pulses. Nonetheless, even with such a pulsed treatment, damage to healthy tissue is frequent, see for example LI Jian-Jun et al. ("Complications of High Intensity Focused Ultrasound for Patients with Hepatocellular Carcinoma", *Technology in cancer research & treatment* 2009, vol. 8, no 3, pp. 217-224 ).

U.S. Pat. No. 6,425,867 teaches a HIFU device with both a scanning and a therapeutic transducer as well as a method for real time ultrasound imaging during HIFU treatment. Synchronization of the therapeutic ultrasonic transducer system relative to the scanning ultrasonic transducer system is provided such that any noise within the imaging data arising from the therapeutic waves is shifted away from the image of the treatment site. Thus, a noise-free image of the treatment site is provided. U.S. Pat. No. 6,425,867 also describes an ultrasound device having synchronization means to synchronize both transducers according to the method.

Such a method provides for good simultaneous imaging of the target area and thus helps focussing the HIFU waves into the target.

WO 03/008041 describes an ultrasound treatment head comprising a probe body which is mounted in rotation around an axis, a treatment transducer with a focussed ultrasound acoustic emission axis which is more or less the same as the probe body rotation axis and an imaging transducer. Such a head has the advantage of implementing treatment and imaging means on the same device. Moreover, the visualization and treatment acoustic axis are more or less the same with the rotation axis, thus ensuring that even when the probe body is rotated, the focal point of the treatment transducer remains at the same spot as well as within the visualization plane of the imaging transducer. Rotation of the probe body is mainly used to acquire images of the target organ or tissue. Treatment of target organs is carried out by shooting short pulses of ultrasound to one spot of the target and then moving on to another spot of the target until the whole target area has been treated.

One big disadvantage of the known ultrasound heads is that even though short pulses are used for HIFU treatment, damage to healthy tissue between the skin and the target organ may still occur.

It is therefore the object of the present invention to avoid the disadvantages of the prior art and to provide for an ultrasound treatment device reducing the heat damage to healthy tissue.

It is another object of the invention to minimize the blanking period, i.e. the cooling phase, thus reducing the overall treatment time.

The invention concerns a device for treatment of an organ or tissue of a living being. The device comprises at least one treatment transducer for emission of ultrasound waves, preferably high intensity focused ultrasound (HIFU) waves, focused on a focal point within or on the surface of said organ or tissue. The device further comprises rotating means to rotate said treatment transducer as well as synchronization means for synchronizing the rotation of the treatment transducer with at least the emission of ultrasound waves from said treatment transducer and/or an additional imaging transducer, whereby the focal point is not moved by the rotation.

"Rotation" as understood herein means a movement around a defined axis. Said movement may be at a constant speed or a changing speed, such as acceleration. Said movement may happen in both directions around said defined axis.

By synchronizing the rotation of the treatment transducer with the emission of ultrasound waves, it is possible to better distribute the heat energy generated by the ultrasound waves from the treatment transducer in the healthy tissue between the transducer and the focal point. Especially in the case of a rectangular transducer or a transducer having an integrated imaging transducer, rotating said transducer during a HIFU pulse or a series of HIFU pulses, while pointing to the same focus, will distribute the heat energy over a greater area while not affecting the energy input in the focal zone. If an imaging transducer is present, emission of ultrasound waves from said imaging transducer are preferably also synchronized with rotation of the treatment transducer.

In one embodiment, the treatment transducer is rotatable about a central propagation axis. For symmetrical transducers, this axis is identical to the symmetry axis of the transducer. The treatment transducer will therefore revolve around itself. The central propagation axis as well as the focal point will not move.

Central propagation axis as used herein is an axis intercepting the centre of the transducer and the focal point. The centre of the transducer as understood herein is the geometrical centre of the surface area of the transducer.

When using a coupling fluid or gel between the transducer and the skin of a patient, there is the possibility of air bubble formation. By rotating the treatment transducer about said central propagation axis with an appropriate speed, such bubbles may be pushed to the edge of the transducer by means of friction forces.

In another embodiment, the treatment transducer is rotatable about an axis which is angled in relation to said central propagation axis and which intersects said focal point. The treatment transducer will therefore follow a precession motion. Since the rotation axis intercepts the focal point, said point will not move. The axis can be angled in any angle <90°, but preferably will be angled in an angle <45°. The angle can be fixed or the device can provide for means of adapting this angle according to treatment need. The adapting means must ensure that the rotation axis will always intersect the central propagation axis of the transducer at the focal point. For example, the transducer may be fixed to an arcuate arm having a rotation axis. By moving the transducer about such an arm it is possible to vary the angle of the central propagation axis of the transducer to the rotation axis.

In yet another embodiment, the treatment transducer is rotatable about an axis which is perpendicular to said central propagation axis and which intersects said focal point. The treatment transducer will therefore follow a tilting or pivoting motion. Since the rotation axis intercepts the focal point, said point will not move. For example, the device can comprise an arcuate holder on which the treatment transducer may be moved back and forth.

In a further embodiment, additionally to being rotatable around an angled or perpendicular axis, the probe head is also rotatable around the central propagation axis. Such an embodiment with a probe head with two rotation axis can further reduce unwanted heat generation outside of the target area. Preferably, rotation about both axes is synchronized with emission of treatment and/or imaging ultrasound waves.

Alternatively, the space between a membrane covering the probe head may be filled with varying volumes of a coupling and/or cooling liquid. By increasing the pressure of the liquid, the membrane will bulge out thus increasing the volume of liquid between the skin of the patient and the transducer, thus moving the focal point. Such a pressure increase as well as a pressure decrease can be synchronized with the rotation and/or the emission of ultrasound waves. Such an embodiment allows for treatment of a target area with varying depth with reduced risk of heat induced damages to healthy tissue.

The treatment device preferably further comprises an imaging transducer, such as an ultrasound probe. This imaging transducer is thereby co-rotatable with the treatment transducer and has an imaging plane intersecting the focal point of the treatment transducer.

Integration of an additional imaging transducer with an imaging plane intersecting the focal point of the treatment transducer allows acquiring images from the target area during treatment. The imaging transducer may be of any suitable kind, such as X-ray, but is preferably an ultrasound probe.

Having a co-rotatable imaging transducer offers the possibility to acquire multiple images during rotation of the transducer which may be processed into a 3-dimensional representation of the target area. Synchronization between the rotation and the imaging frame rate will allow the 3-dimensional representation to be true to the shape of the object. The generation of the 3-dimensional representation requires information about the angular position of the transducer for every processed 2-dimensional image. Therefore, the treatment device preferably comprises additional means to determine the angular position of the transducer and to transmit said position information along with the imaging data.

Further, if a co-rotatable imaging transducer has an imaging plane which includes said rotation axis it may also be used to detect and/or compensate patient motion when rotated around said rotation axis The rotation axis may be represented as a line in the imaging plane. The ultrasound signal along this line remains constant throughout the rotation if no motion occurs, so that changes in the signal may be interpreted as a sign of unwanted motion.

Further, the treatment device may comprise means for generating a 3-dimensional image based on 2-dimensional images acquired by the imaging transducer during rotation. Multiple images acquired during rotation of the transducer may be assembled and processed to a 3-dimensional representation of the target area.

Generally tissue motion occurs in a plane. For example, respiratory motion occurs in the sagittal plane. If motion occurs, the 3-dimensional representation of the object calculated from images acquired during the rotation will be distorted. A correction scheme is described hereafter. Preferably, at least one image is taken in the direction of the plane of motion before the beginning of the treatment. During treatment, signals from the line representing the rotation axis are compared with signals from lines parallel to the line representing the parallel axis from the at least one image taken before the beginning of the treatment. This allows to detect any displacement of signals. This displacement information can be used to correct the acquired image thus yielding an undistorted 3-dimensional image.

Having a 3-dimensional representation of the target area can help monitor the treatment and assess its efficacy. It may also be used to determine the next spot to which the focal point has to be directed to. 3D representation also helps the practitioner to identify the target, to better compare size and aspect of the target before and after the HIFU treatment.

In one embodiment of the invention, a 3-dimensional representation of the target area is further processed in order to compare its actual position relative to a previously acquired 3-dimensional representation. This processing allows to determine a displacement estimator of the target area.

The displacement estimator is then used to determine whether the focal point of the ultrasound is still within the target area. If this is not the case, an appropriate warning may be given. Preferably, the treatment device is provided with means to input a maximal displacement value prior to treatment. If the displacement estimator exceeds this value during treatment, the device may warn the operator.

In another complementary embodiment of the invention, the treatment and imaging transducer, along with the rotation means, are mounted on a robotic table allowing for certain degrees of freedom of the transducer.

Displacement estimation can be used to compute commands for the robotic table in order to realign the focal point within the target area.

In another preferred embodiment of the invention, displacement estimation is performed during HIFU treatment itself by synchronizing the pulses of treatment and imaging ultrasound with rotation of the transducers. The treatment device additionally provides means to interrupt the emission of treatment ultrasound if the focal point moves out of the target area and/or to realign the focal point with the target area by means of the robotic table.

Alternatively, calculation of displacement estimates may be done using a very sparse representation of the target area, starting from only two 2-dimensional images.

As an alternative, the displacement estimator may be calculated in a progressive way, using data from 2-dimensional images sequentially acquired during treatment to improve the accuracy of the displacement estimator.

Another aspect of the present invention is directed to a method for operating a treatment device having a rotatable treatment transducer.

The method comprises the steps of:

Emission of an ultrasound pulse from a treatment transducer being focused on a focal point within or on the surface of said organ and/or tissue; and rotating the treatment transducer in such a way that said focal point is not moved.

Synchronization means thereby synchronize the rotation of the treatment transducer with the emission of the ultrasound pulse.

The synchronization means are preferably in the form of an integrated circuit comprising a microchip or in the form of a computer, such as a workstation or a microcomputer. The synchronization means more preferably further comprise input means such as to allow an operator to change certain parameters or to chose a specific mode of synchronization.

By rotating the treatment transducer during emission of the ultrasound pulse while directing the energy to the same focus, heat energy is more homogenously distributed in the tissue located between the transducer and the focal point. This is especially true in the case of rectangular transducers or transducers having integrated imaging transducers. For example, if a rectangular transducer is rotated by 90° in one direction around the rotation axis during an ultrasound pulse, the area of healthy tissue above the focal point affected by the ultrasonic waves will be greater than if the transducer was not rotated. Thus the heating energy absorbed by the healthy tissue is distributed over a larger volume resulting in less temperature increase and thus less damage. On the other hand, the amount of ultrasound energy reaching the focal point is not affected.

In one embodiment, the treatment transducer is rotated about the central propagation axis of the transducer. In other words, the treatment transducer will revolve around itself. Thereby the central propagation axis as well as the focal point will not move.

In another embodiment, the treatment transducer is rotated about an axis which is perpendicular to said central propagation axis and which intersects said focal point. The treatment transducer will therefore follow a tilting motion. Since the rotation axis intercepts the focal point, said point will not move.

In yet another embodiment, the treatment transducer is rotated about an axis which is angled in relation to said central propagation axis and which intersects said focal point. The treatment transducer will therefore follow a precession motion. Since the rotation axis intercepts the focal point, said focal point will not move.

An integrated imaging transducer will in most cases be arranged somewhere on or within the treatment transducer, thereby creating an area where no treatment ultrasound waves will be generated or where they will be masked. By rotating the treatment transducer, this area will also be rotated. This will subject tissue which would have been shielded by this area to be also subject to ultrasound emission.

In both exemplary cases this allows distribution of generated heat to a greater area than if there was no rotation, thereby reducing heat damages to healthy tissue.

Additionally, the co-rotatable imaging transducer allows the 3-dimensional acquisition to be less prone to tissue motion. Compared to known acquisition techniques for 3-dimensional ultrasound images which require motion of the ultrasound scanner over the patient's skin, friction forces generated by a co-rotatable imaging transducer are heavily reduced, thus minimizing blurring of images due to tissue displacing.

As an alternative, an additional ultrasound pulse from an imaging transducer maybe emitted. Emission of this imaging pulse is synchronized with at least one of the rotation of said imaging transducer, rotation of said treatment transducer and/or emission of said treatment pulse.

Intermittent imaging pulses allow visualizing the target zone and/or the focal point during treatment. This helps assessing the efficacy of the treatment and finding new points to focus the ultrasound to. Synchronizing these imaging pulses with the rotation of the treatment and/or imaging transducer or with the emission of ultrasound pulses from the treatment transducer allows for optimal acquisition of images.

Further the treatment transducer and/or the imaging transducer is rotated $n*90°$ during one pulse of ultrasound. n is thereby any number >0.

If the treatment transducer is rotated about the central propagation axis or about an axis angled to the central propagation axis, n is preferably any integer >0, such as 1, 2, 3, 4 etc. But n may also be any floating-point number such as 0.75, 1.5, 2.2 etc. Most preferably n is 1, 2 or 4, resulting in a respective rotation of the head by 90°, 180° or 360° during one ultrasound pulse. By rotating the treatment transducer during one pulse, heat generation within healthy tissue is reduced thereby minimizing the risk of injury to it.

Alternatively, the treatment transducer may be rotated by $n*90°$ in one direction around the rotation axis and back to its initial position during one pulse. Preferably n is any integer >0, such as 1, 2, 3, 4 etc. But n may also be any floating-point number such as 0.75, 1.5, 2.2 etc. Most preferably n is 1, 2 or 4, resulting in a respective rotation of the head by 90°, 180° or 360° in one direction and back to its initial position during one pulse.

A further alternative is that m ultrasound pulses are emitted from the treatment transducer and/or the imaging transducer during one rotation through 90°.

Preferably m is any integer >0, such as 1, 2, 3, 4 etc. In a preferred embodiment m is 16, resulting in the emission of 16 pulses during rotation of the head by 90°. By applying pulses during rotation through 90°, heat induced injury to healthy tissue is further minimized, since in addition to better heat distribution, the healthy tissue is allowed to shortly cool in between the pulses.

In the case where the treatment transducer is rotated about an axis which is perpendicular to the central propagation axis and which intersects the focal point, the treatment transducer may be rotated about 45° in each direction. During one pulse, the transducer may move from a predefined angle to a second predefined angle. In another embodiment, the ultrasound pulse is emitted while the probe head moves from the first predefined angle to the second predefined angle and back during one pulse. Alternatively, during the motions described above, a multitude of pulses may be emitted.

Further, between each pulse from the treatment transducer one pulse or a series of pulses from the imaging transducer may be emitted. This allows for acquisition of multiple images during rotation, which may be processed to a 3-dimensional representation of the target area and/or the area around the focal point.

Alternatively, the rotation speed of the head and/or pulse emission can be optimized in view of the characteristic cooling rate of the treated tissue. For example, if the treated tissue has a characteristic cooling rate of 30 s—meaning that the over-temperature is reduced by roughly ⅔ after 30 s—rotation of the head and/or emission of ultrasound can be synchronized in such a way that any volume of tissue outside of the focal point is not subjected to treatment waves for at least 30 s.

In another alternative embodiment, skin temperature is monitored, e.g. with an infrared thermometer or with ultrasonic thermography, and rotation and/or emission of ultrasound is synchronized in such a way that the skin temperature does not increase above a certain value. As a further embodiment, the rate of temperature increase and decrease can be monitored and the rotation and/or emission of ultrasound waves synchronized according to the measured temperature changes.

Alternatively, the average acoustic intensity of the waves is mapped over the surface of the transducer, thereby approximating the actual exposure of tissue to ultrasound energy. Rotation of the head can then be synchronized to the emission of ultrasound in such a way that a certain average acoustic intensity is not exceeded.

Further this invention also provides for a treatment method for an organ or tissue by irradiating said organ or tissue with ultrasound pulses from a treatment device as described.

This treatment method provides for a non-invasive ablation treatment of an organ or tissue, thereby minimizing the risk for the patient. Moreover injury to healthy tissue between the treatment transducer and the focal point is reduced in comparison with known HIFU treatments, therefore further minimizing the risks for the patient.

Preferably this method is used to treat the thyroid gland, the parathyroid glands, the breast, the uterus or the prostate.

Further details and benefits of the present invention will be apparent from the following figures and examples:

FIG. 1 shows an embodiment of a treatment device 1 according to the present invention. The treatment device 1 comprises a probe head 2 with central propagation axis 8. Probe head 2 comprises a treatment transducer 3 and an imaging transducer 4, both of which are incorporated into probe head 2. A membrane 5 is wrapped around the probe head 2. The space between membrane 5 and probe head 2 may contain a cooling and/or a coupling liquid. The amount on cooling and/or coupling liquid may be used to adjust the distance between treatment transducer 3 and the tissue to be treated or the skin 27 of a patient. Adjustment of this distance allows for movement of focal point 7 along central propagation axis 8. Focal point 7 lies in the target area 6, which usually will be cancerous cells or a tumour. In this embodiment rotation axis 29 is identical to the central propagation axis 8 of probe head 2. To avoid a shift of focal point 7 during rotation, rotation axis 29 intersects focal point 7. In this embodiment treatment transducer 3 is a HIFU transducer having a concave and spherical configuration, thereby focusing the emission of treatment ultrasound waves 9 towards focal point 7. Treatment transducer 3 may also have any other suitable shape allowing focusing the emission of treatment ultrasound waves 9 towards focal point 7. Further, in this embodiment, imaging transducer 4 is arranged within the concave sphere of treatment transducer 3 symmetrical to central propagation axis 8. Imaging transducer 4 is of rectangular shape. Imaging waves 10 encompass focal point 7, but preferably imaging transducer 4 is configured to acquire images along the entire diameter of the spherical treatment transducer 3.

Figure 1:
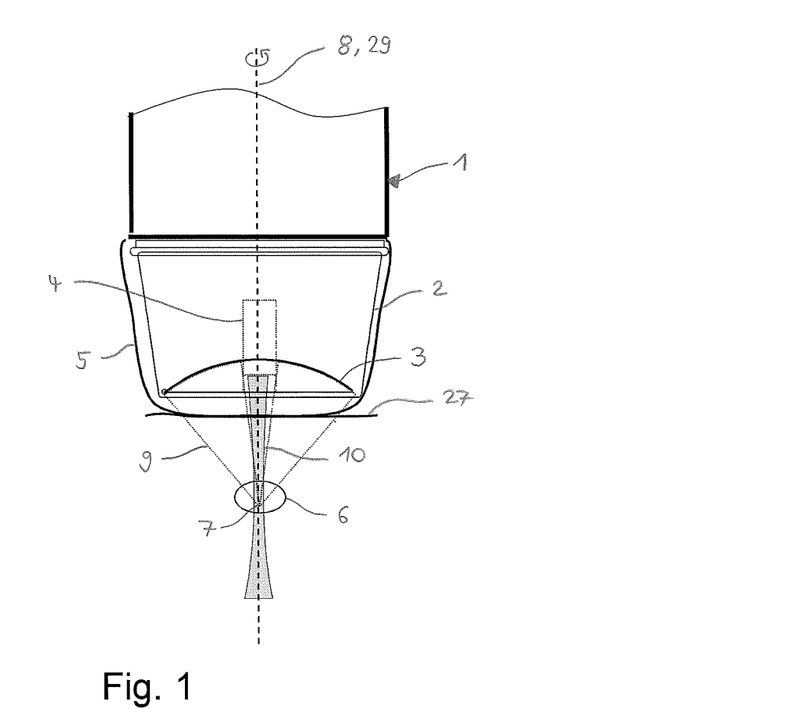
FIG. 1: An embodiment of a treatment device according to the present invention where the rotation axis is identical with the central propagation axis
Figure 2A:
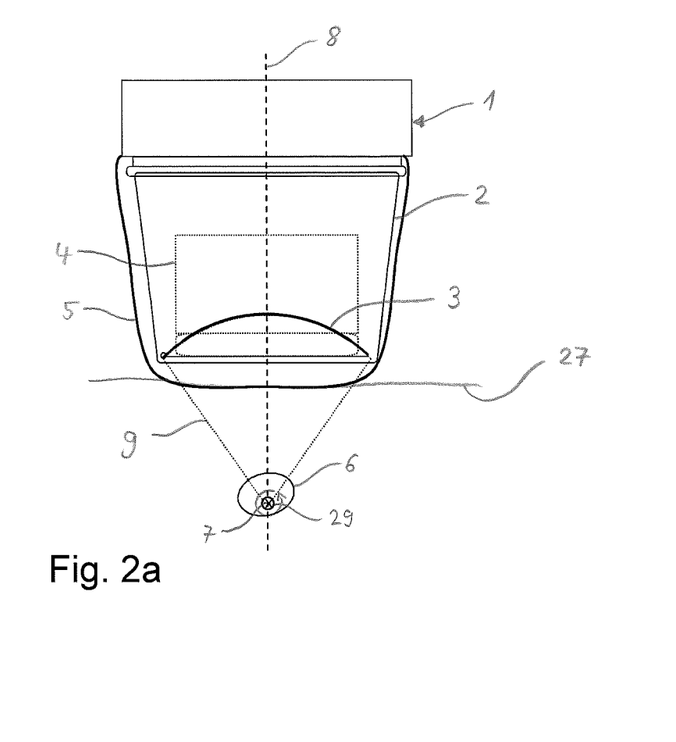
FIG. 2a: Another embodiment of the treatment device with a rotation axis which is perpendicular to the central propagation axis
Figure 2B:
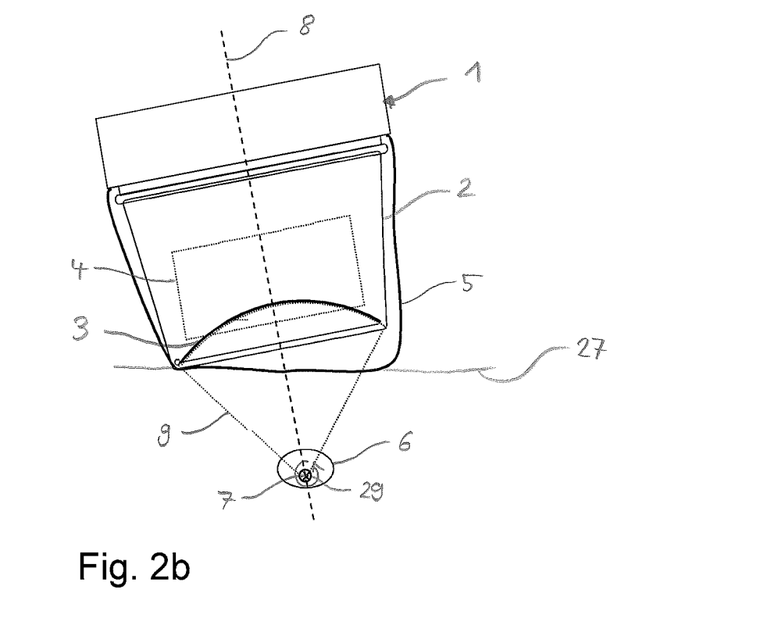
FIG. 2b: The treatment device of FIG. 2a rotated about a certain angle

On FIGS. 2a and 2b a second embodiment of a treatment device 1 according to the present invention is shown. In this embodiment, rotation axis 29 is perpendicular to central propagation axis 8. FIG. 2a shows the probe head 2 in neutral position. FIG. 2b shows probe head 2 rotated about a certain predefined angle around rotation axis 29. Since rotation axis 29 intercepts focal point 7, focal point 7 does not move during rotation of probe head 2. In the representation, rotation axis 29 is perpendicular to the plane of the figure. Alternatively, rotation axis 29 can have any other suitable orientation. However, for the focal point 7 not to move during rotation, rotation axis 29 must always intercept focal point 7. Probe head 2 may be rotated to any angle in both directions around axis 29. For practical reasons, probe head 2 will preferably not be rotated more than 45° in any direction. One treatment ultrasound wave may be emitted during rotation of the probe head from one predefined angle to a second predefined angle. Alternatively, one pulse may be emitted during rotation of the probe head 2 from one predefined angle to a second predefined angle and back to the first angle. Further, during the rotation motions described above, a multitude of pulses may be emitted. Preferably, rotation of the probe head 2 around axis 29 is synchronized with emission of treatment ultrasound waves from transducer 3 and/or imaging waves from imaging transducer 4. Preferably the plane of imaging is perpendicular to the rotation axis.

Figure 3:
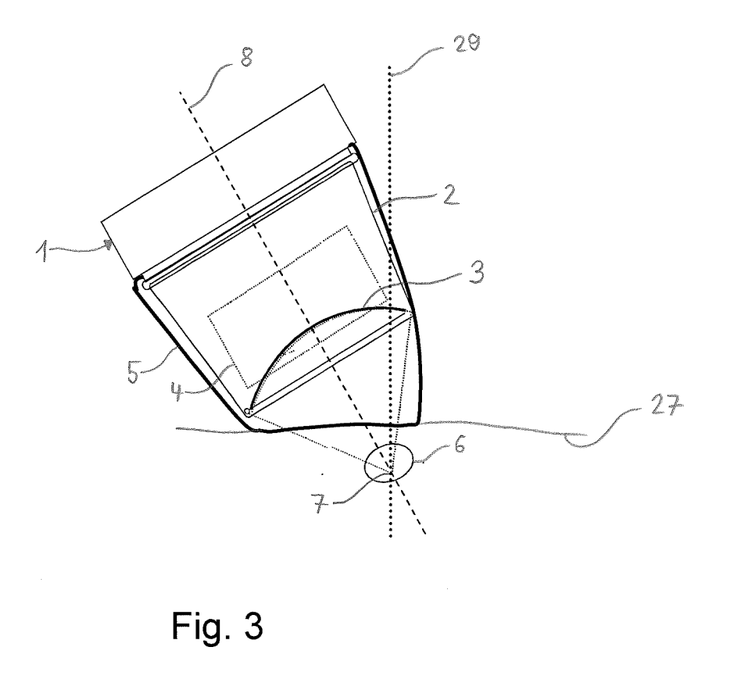
FIG. 3: A further embodiment of the treatment device having a rotation axis which is angled in relation to the central propagation axis

FIG. 3 shows yet another embodiment of a treatment device 1 of the present invention. In this embodiment, probe head 2 is rotated about a rotation axis 29 which is angled in relation to the central propagation axis 8. Probe head 2 will therefore follow a precession motion around axis 29. Since rotation axis 29 intercepts focal point 7, said focal point 7 will not move during rotation of probe head 2. Preferably, probe head 2 is thereby mounted on an arcuate arm encompassing the rotation axis 29. Probe head 2 may be slidably mounted on said arm, such that the angle may be varied depending on the tissue and/or organ to be treated. Alternatively, probe head 2 may be moved about said arm during rotation about said axis, resulting in a coupled rotation about two axes. Such motions must be synchronized as well as synchronized to the emission of treatment as well as imaging waves.

Figure 4A:
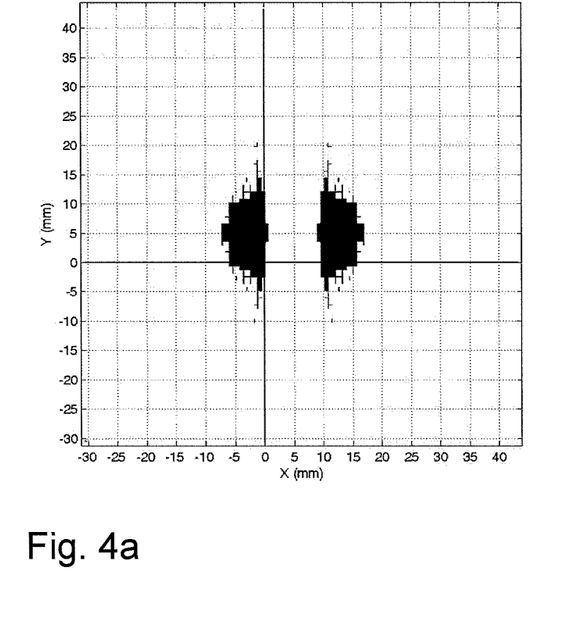
FIG. 4a: Simulated heat distribution on the surface of a patient's skin without rotation of the treatment transducer
Figure 4B:
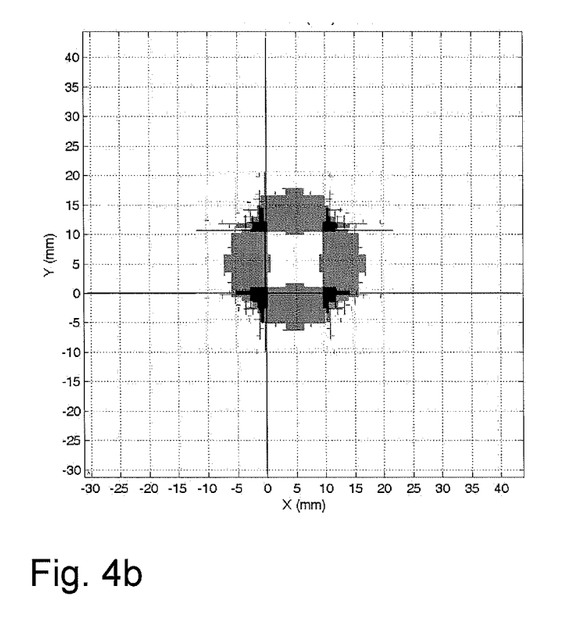
FIG. 4b: Simulated heat distribution on the surface of a patient's skin with rotation of the treatment transducer

On FIGS. 4a and 4b simulated heat distribution on the skin of a patient is represented. Darker shades represent higher temperatures. Both half circles seen on FIG. 4a represent the heat generated by treatment ultrasound waves when the transducer is not rotated. The white area in between both half circles is the location of the imaging transducer, which was simulated to have a rectangular shape stretching over the entire diameter of the circularly shaped treatment transducer. FIG. 4b represents the heat distribution when the treatment transducer is rotated by 90° during emission of a treatment ultrasound pulse. As is readily apparent, heat is now distributed more homogenously over the entire circular area of the treatment transducer. This considerably reduces the risk of heat induced damages to healthy tissue between the transducer and the focal point.

Figure 5:
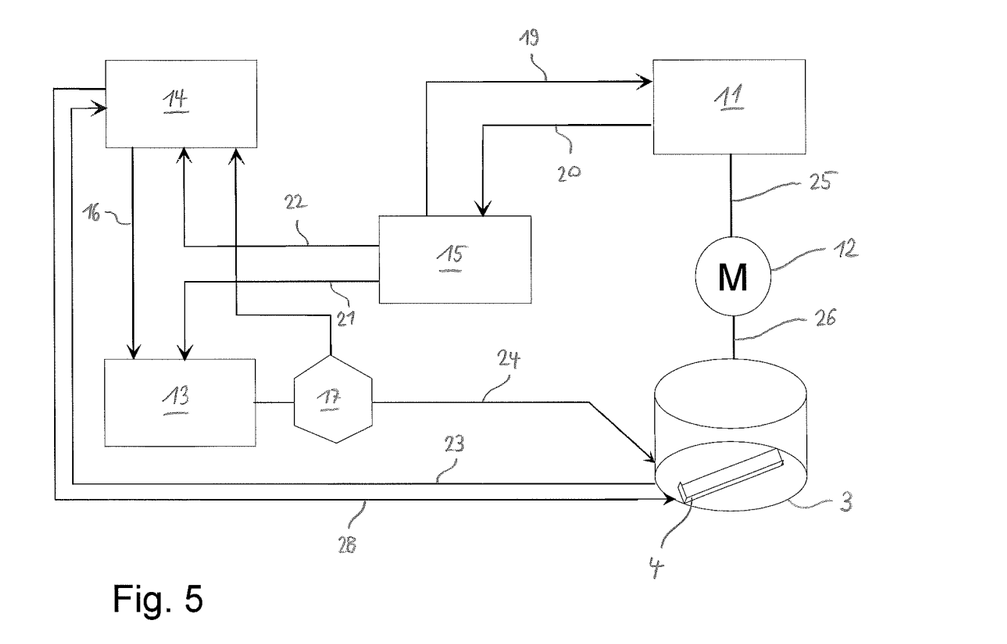
FIG. 5: Schematic representation of the control and synchronization arrangements of a treatment device

FIG. 5 shows a schematic representation of a treatment device according to the present invention. Probe head 2 comprises treatment transducer 3 and imaging transducer 4. Motor 12 is coupled to probe head 3 via coupling 26. Coupling 26 preferably is a direct mechanical coupling, but may alternatively also be in the form of a gear, such as a worm gear or the like. Head rotation controller 11 provides motor rotation signals 25 to motor 12 and transmits information about head position 20, especially the angular position of the transducers, to central control unit 15. Central control unit 15 comprises a user interface as well as synchronization means for the rotation of the probe head 2 and emission of both treatment transducer 3 and imaging transducer 4. Preferably central control unit 15 comprises a computer or similar electronic control device and a user interface device such as keyboard, mouse and/or trackball. Preferably it further comprises an optical output device such as a screen. Central control unit 15 provides imaging scanner control signals 22 to ultrasound imaging scanner 14 as well as treatment ultrasound control signals 21 to frequency generator 13.

Used frequencies for the treatment waves are in the range of 1 to 20 MHz, preferably 1-3 MHz. Frequencies generated in generator 13 are transmitted to treatment transducer 3 via power cable 24. Treatment transducer 3 then generates HIFU treatment waves. Ultrasound imaging scanner 14 controls imaging transducer 4 via imaging control signal 28. Imaging signals 23 are transmitted back to ultrasound imaging scanner 14, which processes the signals to a 2-dimensional representation which may in turn be displayed on the optical output device of central control unit 15. Control and synchronization of rotation of probe head 2, acquisition of imaging data as well as generation of HIFU treatment waves is done by central control unit 15. Alternatively, synchronization between imaging and emission of HIFU treatment waves could be achieved by means of a power detector 17 providing a gating signal 18 to ultrasound imaging scanner 14 when frequencies are transmitted to treatment transducer 3 via power cable 24, said gating signal preventing ultrasound imaging scanner 14 to acquire images. As a further alternative, ultrasound imaging scanner 14 provides a gating signal to radiofrequency generator 13 during image acquisition to prevent emission of HIFU treatment waves.

The treatment device according to the present invention may exemplarily be used for the ablation of an enlarged parathyroid gland. The method may comprise the following steps:

the treatment head is positioned on the patient neck, such that the focal point is located at the center of the parathyroid gland

[the treatment head is rotated around its axis so that the image plane is oriented sagitally to the patient]

The treatment transducer emits a 3 MHz, 25 W acoustic wave, concentrated on the focal point, during 8 s In synchronization, with the pulse, the treatment head is made to rotate 90° C. around its axis during the 8 seconds The treatment head is moved 2 mm sideways and rotated back by −90°

Steps c) to e) are repeated until the whole gland is treated

Alternatively, another exemplary method of treatment using the treatment device according to the present invention may comprise the following steps:

the treatment head is positioned on the patient neck, such that the focal point is located at the center of the parathyroid gland A series of 17 images is recorded, rotating the head by a known angle of 180°/16=11.25° between the images and starting with an image taken in the sagittal plane A 3 dimensional representation of the target is calculated from the recorded images The head is rotated back by −180°

The treatment transducer emits a 8 s, 3 MHz, 25 W concentrated acoustic waves.

the head is rotated by 11.25° and an ultrasound image is taken the ultrasound image is compared to the 3 dimensional representation. If unwanted motion has occurred, the head is translated to compensate for that motion the head is translated by 2 mm so the focal point is located next to the first position Steps e) to h) are repeated until the whole gland is treated

The invention claimed is:

1. A device for treatment of an organ or tissue of a living being, said device comprising:
    at least one treatment transducer rotatably mounted around an axis, said transducer being adapted for emission of high intensity focused (HIFU) ultrasound waves,
    said ultrasound waves being focused on a focal point within or on the surface of said organ or tissue; and
    means for rotating said treatment transducer around said axis, wherein said axis intersects the focal point, such that a rotation of the treatment transducer around the axis does not move the focal point and
    wherein the device further comprises synchronization means for synchronizing the rotation of the treatment transducer with at least the emission of ultrasound waves of at least one of said treatment transducer and an imaging transducer.

2. The device according to claim 1, wherein said treatment transducer is rotatable about an axis which is identical with a central propagation axis of said transducer.

3. The device according to claim 1, wherein said treatment transducer is rotatable about an axis which is perpendicular to a central propagation axis of said transducer and which intersects said focal point.

4. The device according to claim 1, wherein said treatment transducer is rotatable about an axis which is angled in relation to a central propagation axis of said transducer and which intersects said focal point.

5. The device according to claim 1, wherein an additional imaging transducer is co-rotatable with said treatment transducer and has an imaging plane intersecting the focal point of said treatment transducer.

6. A device according to claim 5, wherein the additional imaging transducer is an ultrasound probe.

* * * * *